(12) United States Patent
Asjes

(10) Patent No.: US 6,614,029 B2
(45) Date of Patent: Sep. 2, 2003

(54) ELECTROSTATIC MANIPULATING APPARATUS

(75) Inventor: Ronald Jan Asjes, Eindhoven (NL)

(73) Assignee: FEI Company, Hillsboro, OR (US)

(*) Notice: Subject to any disclaimer, the term of this patent is extended or adjusted under 35 U.S.C. 154(b) by 0 days.

(21) Appl. No.: 10/252,845

(22) Filed: Sep. 23, 2002

(65) Prior Publication Data

US 2003/0089860 A1 May 15, 2003

(30) Foreign Application Priority Data

Sep. 24, 2001 (EP) .............................. 01203610

(51) Int. Cl.⁷ .............................................. H01J 37/205
(52) U.S. Cl. ................. 250/442.11; 250/310; 250/311; 250/306; 250/492.1; 250/492.2; 324/158 R; 324/158 D; 324/501
(58) Field of Search ........................... 250/442.11, 310, 250/311, 306, 492.1–492.2; 324/158 R, 158 D, 501

(56) References Cited

U.S. PATENT DOCUMENTS 5,270,552 A 12/1993 Ohnishi et al. ............. 250/307
6,538,254 B1 * 3/2003 Tomimatsu et al. ..... 250/442.11

FOREIGN PATENT DOCUMENTS

EP 0 927 880 A1 7/1999 ............ G01N/1/28

* cited by examiner

Primary Examiner—John R. Lee
Assistant Examiner—Zia R. Hashmi
(74) Attorney, Agent, or Firm—Michael O. Scheinberg

(57) ABSTRACT

An electrostatic manipulating apparatus for handling a sample (1) during and after removal from semiconductor wafers (3) under a continuous vacuum, comprising a fork (7) of at least two electrically conductive elements (10) capable of exerting an electrostatic force on said sample. Preferably all electrically conductive elements are covered by a thin coating of insulating material for improved contact and release.

14 Claims, 3 Drawing Sheets

ELECTROSTATIC MANIPULATING APPARATUS

BACKGROUND OF THE INVENTION

The invention relates to an electrostatic manipulating apparatus.

For transmission electron microscope (TEM) analysis, micro-samples are removed from semiconductor wafers by a combination of a scanning electron microscope (SEM) and focused ion beam (FIB). This is realized with a focused ion beam to cut the sample and a SEM for determination of the location of the region of interest. Subsequently the samples are taken outside the vacuum chamber and placed under an optical microscope on a TEM sample holder. The size of the samples is usually about 15 to 20 $\mu$m×5 $\mu$m×0.1 to 1 $\mu$m. This is a rather time-consuming operation in which samples may be damaged or get lost.

In order to increase the reliability and the productivity an automated sampling apparatus would be desirable, that will perform all required operations under one and the same vacuum, thus avoiding any possible effects of being exposed to the atmosphere (in particular oxygen, water vapour and the like). In addition such an automatic apparatus would permit a more accurate action and a faster production.

In U.S. Pat. No. 5,270,552 it is described that a micro-sample may be removed from a wafer by means of a fine probe which is attached to the sample by a beam-induced deposition film. This method has the disadvantage that the deposition film introduces a possible contaminant which is undesirable in the semiconductor fabrication environment. Moreover, a fine probe is very fragile and susceptible to damage by collision with the wafer or sample surface.

European Patent Application EP 0 927 880 A1 describes a method and apparatus for preparing samples whereby, as illustrated by FIG. 13, a probe is firmly joined to a micro-specimen by using an electrostatic absorption technique. In this respect it is observed that said method has the merit that there is no accompanying chemical change in quality and that no accompanying contamination is introduced in the wafer or the sample. However, it has a significant disadvantage due to the fact that the position and orientation of the sample, once attached to the probe, is undefined. As a consequence, serious difficulties are encountered in attempting to attach the sample to a support in such a way that it is suitable for TEM observation and analysis.

The present inventor has recognized that advantages may be attained by handling samples in a stable, fully controlled manner, thus allowing a stable procedure. The inventor has also recognized that in addition the procedure might be automated, thus providing a substantial advantage over any prior art method.

SUMMARY OF THE INVENTION

In consequence, amongst other things, it is an object of the invention to provide an apparatus for handling a sample during and after removal from semiconductor wafers under a continuous vacuum without introducing foreign material while the sample is maintained in a stable position. Therefore, according to one of its aspects the invention is characterized in conformity with the characterizing part of claim 1. Further advantageous aspects of the invention are disclosed in the dependent claims.

BRIEF DESCRIPTION OF THE DRAWING

These and further aspects and advantages of the invention will be discussed more in detail hereinafter in the description of preferred embodiments, in particular with reference to the appended Figures, wherein.

GENERAL CONSIDERATIONS

Figure 1:
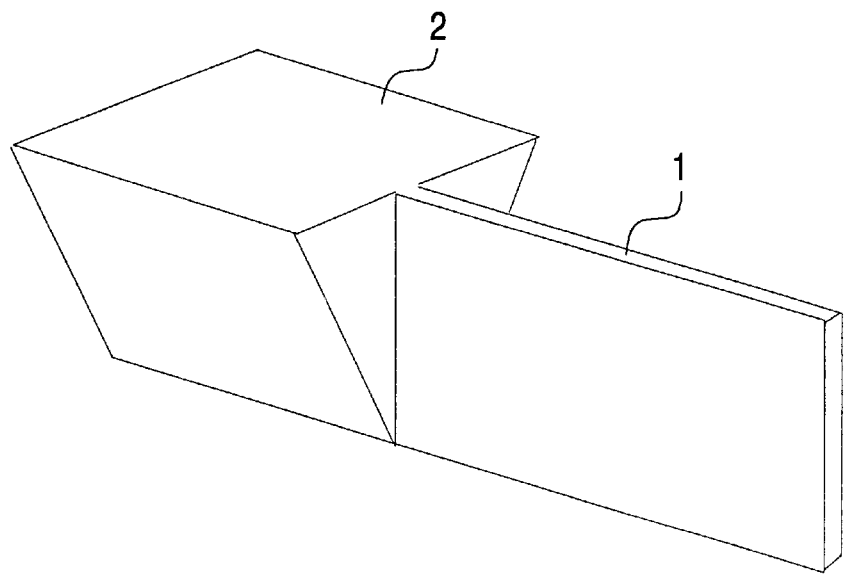
FIG. 1 shows a preferred embodiment of a micro-sample which includes a larger region at one side whereto a manipulator can be attached.

With respect to considering the apparatus according to the present invention, comprising a fork of at least two electrically conductive elements capable of exerting an electrostatic force on a sample, the inventor has recognized that use of electrostatic forces avoids possible contamination by foreign material while the sample is held in position. The inventor has also realized that the net charge of the object to be handled will stay zero by providing the surfaces of the electrically conductive elements with an insulating layer. Thus, two conductive elements will acquire opposite charges and the net charge of the object will remain zero. The inventor has also realized that the sample can be disconnected from the apparatus by removing the applied voltage, if desired, by application of a reverse polarity.

DETAILED DESCRIPTION OF PREFERRED EMBODIMENTS

The present invention will be elucidated in the following detailed description of some preferred embodiments as given with reference to the accompanying drawings. In the drawings FIGS. 1 and 2 refer to preferred embodiments of a micro-sample, while FIGS. 3 to 6 refer to an apparatus for handling such micro-samples and also those which have been released from a wafer in a known manner such as described, for example, in EP 0 927 880.

FIG. 1 shows a micro-sample (1) made by FIB cutting with an additional mechanical support (2) for handling by means of a manipulator. The actual dimensions of the micro-sample are about 20 $\mu$m×5 $\mu$m×0.1 to 1 $\mu$m. As a consequence of the fragility and small dimensions of the micro-sample parallel to the wafer surface, it is advantageous to have a larger and more robust part on the micro-sample. The dimensions of the top (wafer) surface of this part are about 10 $\mu$m×5 $\mu$m. Larger dimensions are possible but will demand a longer period of time for the preparation of the micro-sample, thus reducing the throughput efficiency.

Figure 2:
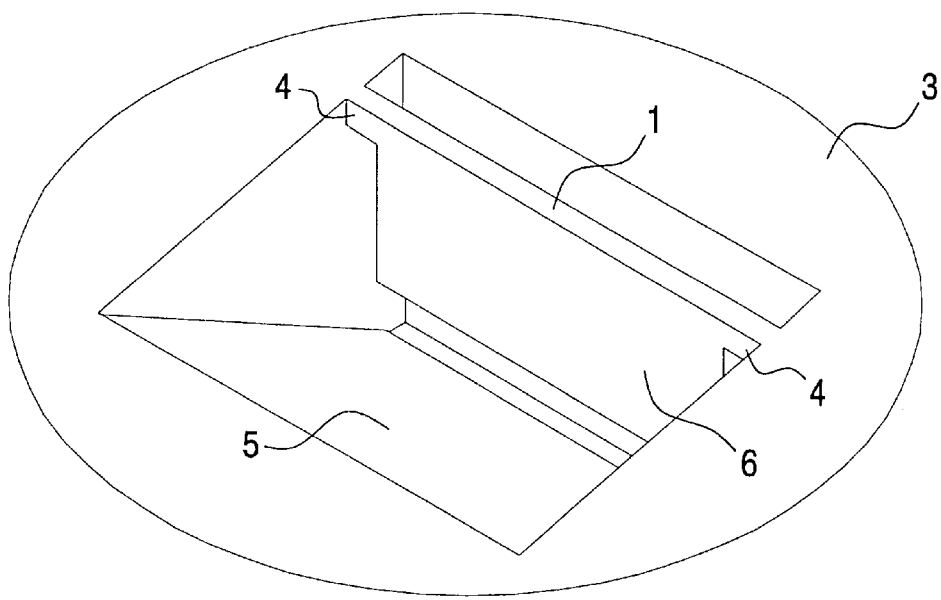
FIG. 2 shows a second preferred embodiment of a micro-sample after milling out holes in the wafer on either side and around its perimeter, except at two positions, holding the sample in place in the wafer.

FIG. 2 shows a detail of a wafer (3) with a micro-sample (1) still located in its pit, without any mechanical parts. With the exception of two positions at its top edges (4) it has been cut free by a FIB. The dimensions of this micro-sample are comparable with those in FIG. 1. The big hole with the slanting wall (5) is required to be able to mill the sides and bottom of the micro-sample. The surface (6) of the micro-sample is perpendicular to the surface of the wafer and presents in general the cross section of interest for the analysis.

Figure 3:
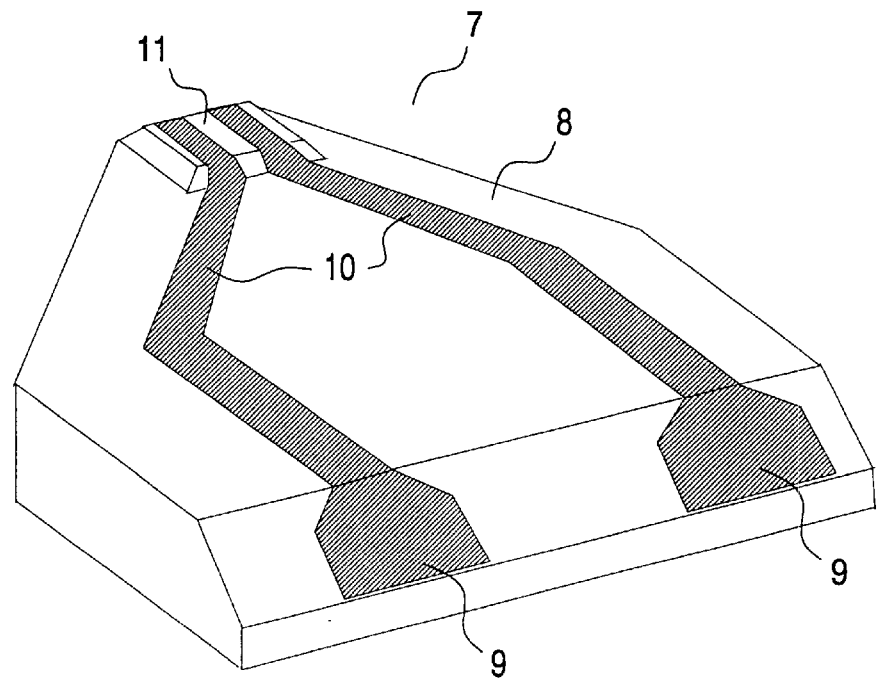
FIG. 3 shows an apparatus for contacting, holding and releasing micro-samples such as a customary membrane that is still in its pit.

Advantages of this way of preparation of a sample are the minimum time required for preparation (FIB milling) and the smallest volume and area removed of the wafer to be analyzed. However, it is more complicated for a manipulator to take the micro-sample out of its pit without damaging or contaminating it. FIG. 3 is a view of an electrostatic manipulating apparatus for handling a sample during and after removal from semiconductor wafers under a continuous vacuum; it comprises a fork of at least two electrically conductive elements capable of exerting an electro-static force on said sample. A sample as shown in FIG. 1 is lifted from its position by means of an apparatus (7) comprising a substrate with a main surface (8), contact areas (9) which are located below the main surface, and electrically conductive elements (10) leading to the mesa surface (11). This mesa surface creates a clearance between the main surface of the substrate and the wafer surface. A voltage via the contact areas will create an electro-static force on the sample, allowing the sample to be lifted and removed from the wafer. If desired or required, the sample can be positioned at the intended location; it is then released by removing the voltage. Occasionally the residual forces between the sample and the apparatus as shown herein such as, for example, electrostatic forces from the (partly) polarized insulating material (electret effect), may still resist separation of the sample from the apparatus. In that case the desired separation can be achieved by means of an alternating voltage with a gradually decreasing amplitude to zero volts.

Figure 4:
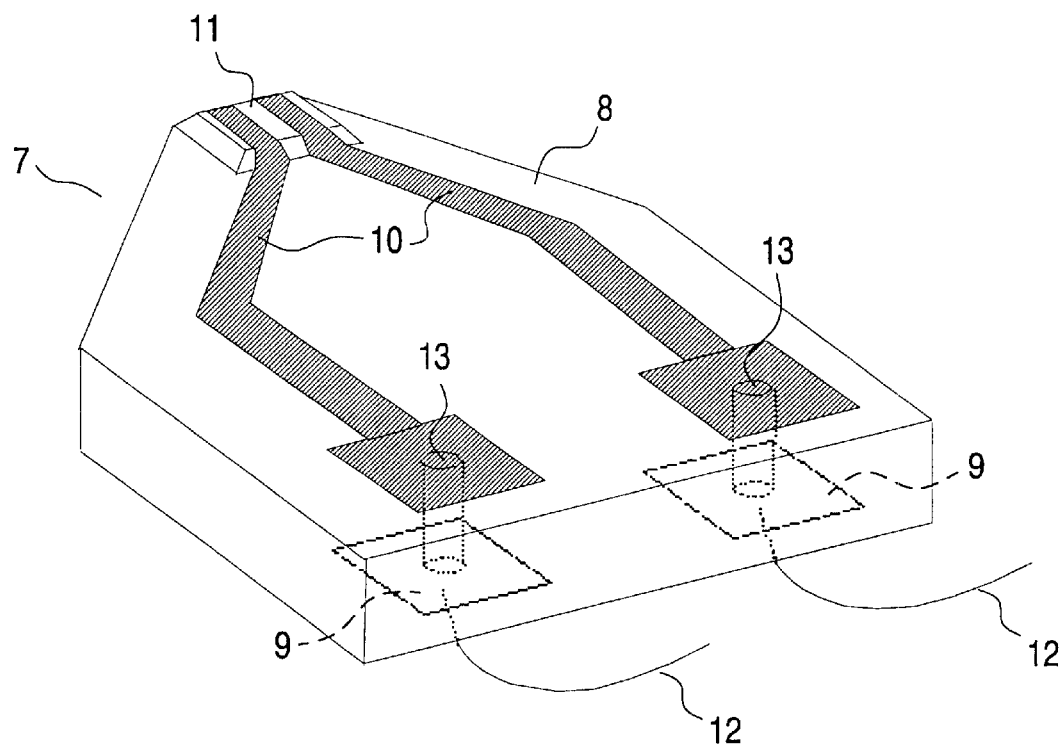
FIG. 4 shows a modified version of the apparatus as shown in FIG. 3.

FIG. 4 shows a modified version of the apparatus as shown in FIG. 3, wherein the contact areas (9) are located at the backside of the substrate. The bonding wires (12) can supply the voltage to the contact areas by isolated vias (13).

Figure 5:
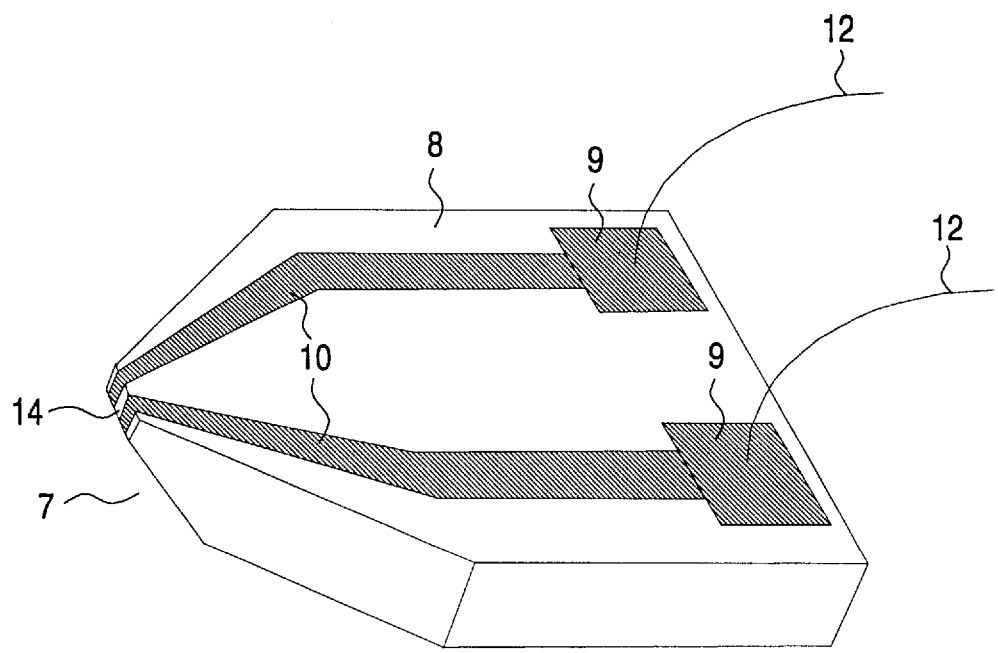
FIG. 5 shows another modified version of the apparatus as shown in FIG. 3.

FIG. 5 shows another modified version of FIG. 3, wherein the bonding wires (12) and the contact areas (9) are both at the main surface and in contact with the electrically conductive elements (10) at the side surface (14).

Figure 6:
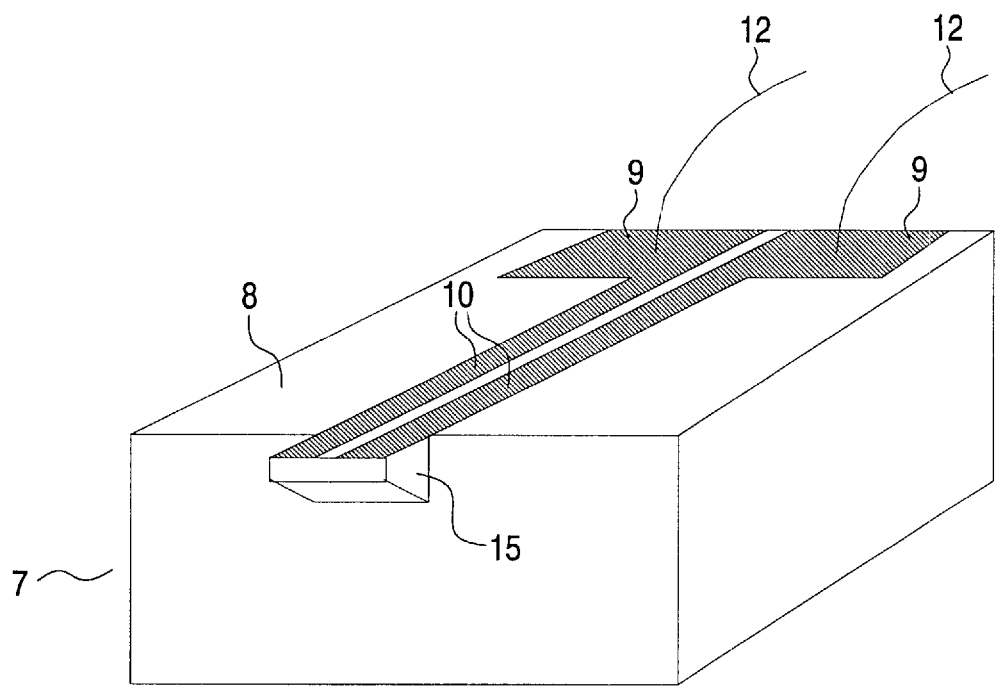
FIG. 6 shows still another modified version of the apparatus as shown in FIG. 3, wherein the electrically conducting elements are prolonged on a surface protruding beyond the main surface.

FIG. 6 shows an apparatus (7) capable of picking up and manipulating samples of the type described in FIG. 2. The electrically conductive elements (10) are prolonged on a protruding surface (15). The dimensions thereof are smaller than those of the big hole with the slanting wall (5) of FIG. 2. It is thus possible to make mechanical contact with the surface (6) of the micro-sample which is perpendicular to the wafer surface.

In all embodiments the surfaces of the electrically conductive elements (10) at the mesa surface (11), the side surface (14) and the protruding surface (15) locations all have a length of about 5 μm and a width of 3 μm.

In all embodiments the surfaces of the electrically conductive elements are, at least on the mesa surface, the side surface and the protruding surface locations, coated with an insulating material which preferably has a high dielectric constant, such as $Ta_2O_5$, but other insulating materials, such as, for example, photoresist, Parylene, Mylar, SiO, $SiO_2$, $Si_3N_4$, $Al_2O_3$, $TiO_2$ are also possible.

In the above embodiments an applied voltage the insulating layer of one finger will be charged positively, while the other will be charged negatively. Thus, there will be an attracting force which will remain constant as the insulating layers will prevent a current flow. As stated earlier, the sample is released by removing the voltage and, if necessary, by applying an alternating voltage of decreasing amplitude in order to redistribute the charge of the insulating material.

The inventor has further provided a method for handling a sample of a semiconductor wafer by means of an apparatus as described above, comprising the steps of:

a) attracting said sample to said fork by electrostatic means, b) cutting said sample loose from said wafer by means of a FIB beam, c) removing said sample from said wafer by means of said fork, d) bringing said sample into contact with an appropriate support medium, e) removing said electrostatic force from said fork, and f) separating said fork from said sample by a relative displacement of the fork with respect to the support.

For convenient handling it is desirable to connect the fork to a micro-manipulator, such as, for example, a piezo-actuator, having at least one degree of freedom.

What is claimed is:

1. An electrostatic manipulating apparatus for handling a micro-sample (1) during and after removal from semiconductor wafers (3) under a continuous vacuum, comprising a fork (7) of at least two electrically conductive elements (10) capable of exerting an electrostatic force on said sample.

2. An apparatus as claimed in claim 1, wherein any electrically conductive element is covered by a thin coating of insulating material.

3. An apparatus as claimed in any one of claims 1 and 2, wherein said fork is connected to a micro-manipulator.

4. An apparatus as claimed in claim 3, wherein said micro-manipulator is a piezo-actuator.

5. An apparatus as claimed in claim 4, wherein said piezo-actuator has a plurality of degrees of freedom.

6. An apparatus as claimed in claim 4, wherein said piezo-actuator has one degree of freedom.

7. An apparatus as claimed in claim 1, wherein said fork is composed of a material comprising silicon (Si).

8. An apparatus as claimed in claim 7, wherein said fork is composed of $SiO_2$.

9. An apparatus as claimed in claim 7, wherein said fork is composed of glass.

10. An apparatus as claimed in any one of the claims 1 and 7, wherein all electrically conductive elements are coated with a thin electrically insulating layer of a material selected from the following: photoresist, Parylene, Mylar, SiO, $SiO_2$, $Si_3N_4$, $Al_2O_3$, $Ta_2O_5$.

11. An apparatus as claimed in any one of claims 1 and 7, wherein all electrically conductive elements are coated with a thin layer of $Ta_2O_5$.

12. An apparatus as claimed in claim 1, wherein the sample acquires a polarity opposite to that of the fork.

13. An apparatus as claimed in claim 1, wherein said electrostatic force is exerted by means of a plurality of voltages applied to said electrically conductive elements.

14. A method for handling a sample (1) of a semiconductor wafer (3) by means of an apparatus as claimed in claim 1, comprising the steps of:

a) attracting said sample to said fork (7) by electrostatic means, b) cutting said sample loose from said wafer by means of a FIB beam, c) removing said sample from said wafer by means of said fork, d) bringing said sample into contact with an appropriate support medium, e) removing said electrostatic force from said fork, and f) separating said fork from said sample by a relative displacement of the fork with respect to the support.

* * * * *